United States Patent [19]

De Francesco et al.

[11] Patent Number: 5,739,002
[45] Date of Patent: Apr. 14, 1998

[54] METHOD FOR REPRODUCING IN VITRO THE PROTEOLYTIC ACTIVITY OF THE NS3 PROTEASE OF HEPATITIS C VIRUS (HCV)

[75] Inventors: Raffaele De Francesco; Christina Failla, both of Rome; Licia Tomei, Naples, all of Italy

[73] Assignee: Istituto di Richerche di Biologia Molecolare P. Angeletti S.p.A., Pomezia RM, Italy

[21] Appl. No.: 700,356
[22] PCT Filed: Feb. 14, 1995
[86] PCT No.: PCT/IT95/00018
  § 371 Date: Aug. 23, 1996
  § 102(e) Date: Aug. 23, 1996
[87] PCT Pub. No.: WO95/22985
  PCT Pub. Date: Aug. 31, 1995

[30] Foreign Application Priority Data

Feb. 23, 1994 [IT] Italy ................. RM94A0092

[51] Int. Cl.$^6$ ............... C12Q 1/37; C12Q 1/70; C12N 9/50; C07H 21/04
[52] U.S. Cl. ............... 435/23; 435/5; 435/7.6; 435/219; 536/23.2; 536/23.72
[58] Field of Search ............... 435/5, 23, 24, 435/219, 6, 7.6; 536/23.2, 23.72

[56] References Cited

PUBLICATIONS

Grakoui et al. (1993) J. Virology 67, No.5, 2832–2843.
Journal of Virology, vol. 68, No. 6, 1994, pp. 3753–3760. C. Fatilla et al., "Both NS3 and NS4 are required for Proteolytic processing of HCV nonstructural proteins."

Journal of Virology, vol. 67, No. 7, 1993, pp. 4017–4026. L. Tomei et al., "NS3 is a serine protease required for processing of HCV polyprotein."

Virology, vol. 204, 1994, pp. 163–169. S.S. Leinbach et al., "Substrate specificity of the NS3 proteinase of HCV ... ".

Proc. Natl. Acad. Sci. USA, vol. 91, 1994, pp. 888–892. E. Pizzi et al., "Molecular model of the specificity pocket of the HCV protease ... ".

*Primary Examiner*—Robert A. Wax
*Assistant Examiner*—Elizabeth Slobodyansky
*Attorney, Agent, or Firm*—Browdy and Neimark

[57] ABSTRACT

This is a method for reproducing in vitro the serine protease activity associated with the HCV NS3 protein, that comprises using both of the sequences contained in NS3 and the sequences contained in NS4A. This method takes advantage of the ability of the HCV NS4A protein, or sequences contained therein, to act as a cofactor of the serine protease activity or more generally of the enzymatic activities associated with NS3. Optimal serine protease activity is obtained when NS4A is present in a molar ratio of at least 1:1 with NS3. NS3 and NS4A can also be incorporated in the reaction mixture as NS3-NS4A precursor, as this precursor will generate, by means of an autoproteolytic event, equimolar amounts of NS3 and NS4A. It is also possible to mutate the cleavage site between NS3 and NS4A in a precursor, so that NS4A remains covalently The sequences that do not influence the proteolytic activity of NS3 can subsequently be removed from protease activity.

20 Claims, 1 Drawing Sheet

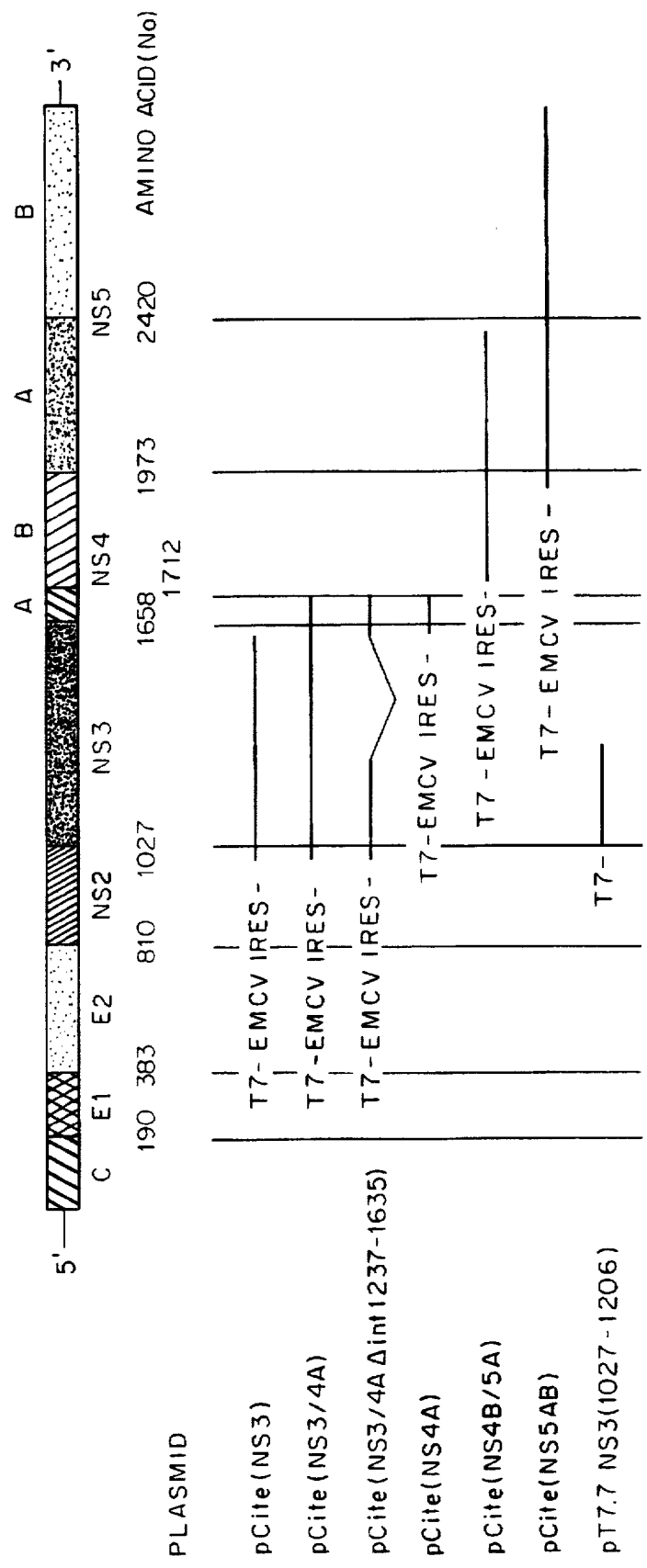

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 631 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Ala  Pro  Ile  Thr  Ala  Tyr  Ser  Gln  Gln  Thr  Arg  Gly  Leu  Leu  Gly  Cys
 1              5                        10                       15

Ile  Ile  Thr  Ser  Leu  Thr  Gly  Arg  Asp  Lys  Asn  Gln  Val  Glu  Gly  Glu
                20                       25                       30

Val  Gln  Val  Val  Ser  Thr  Ala  Thr  Gln  Ser  Phe  Leu  Ala  Thr  Cys  Val
               35                   40                        45

Asn  Gly  Val  Cys  Trp  Thr  Val  Tyr  His  Gly  Ala  Gly  Ser  Lys  Thr  Leu
     50                        55                   60

Ala  Ala  Pro  Lys  Gly  Pro  Ile  Thr  Gln  Met  Tyr  Thr  Asn  Val  Asp  Gln
```

-continued

|  | 65 |  |  |  | 70 |  |  |  | 75 |  |  |  | 80 |  |  |
|---|---|---|---|---|---|---|---|---|---|---|---|---|---|---|---|
| Asp | Leu | Val | Gly | Trp 85 | Pro | Lys | Pro | Pro 90 | Gly | Ala | Arg | Ser | Leu 95 | Thr | Pro |
| Cys | Thr | Cys | Gly 100 | Ser | Ser | Asp | Leu 105 | Tyr | Leu | Val | Thr | Arg 110 | His | Ala | Asp |
| Val | Ile | Pro 115 | Val | Arg | Arg | Arg 120 | Gly | Asp | Ser | Arg | Gly 125 | Ser | Leu | Leu | Ser |
| Pro | Arg 130 | Pro | Val | Ser | Tyr 135 | Leu | Lys | Gly | Ser | Ser 140 | Gly | Gly | Pro | Leu | Leu |
| Cys 145 | Pro | Phe | Gly | His | Ala 150 | Val | Gly | Ile | Phe | Arg 155 | Ala | Ala | Val | Cys | Thr 160 |
| Arg | Gly | Val | Ala | Lys 165 | Ala | Val | Asp | Phe | Val 170 | Pro | Val | Glu | Ser | Met 175 | Glu |
| Thr | Thr | Met | Arg 180 | Ser | Pro | Val | Phe | Thr 185 | Asp | Asn | Ser | Ser | Pro 190 | Pro | Ala |
| Val | Pro | Gln 195 | Ser | Phe | Gln | Val | Ala 200 | His | Leu | His | Ala | Pro 205 | Thr | Gly | Ser |
| Gly | Lys 210 | Ser | Thr | Lys | Val 215 | Pro | Ala | Ala | Tyr | Ala 220 | Ala | Gln | Gly | Tyr | Lys |
| Val 225 | Leu | Val | Leu | Asn | Pro 230 | Ser | Val | Ala | Ala | Thr 235 | Leu | Gly | Phe | Gly | Ala 240 |
| Tyr | Met | Ser | Lys | Ala 245 | His | Gly | Ile | Asp | Pro 250 | Asn | Ile | Arg | Thr | Gly 255 | Val |
| Arg | Thr | Ile | Thr 260 | Thr | Gly | Ala | Pro | Val 265 | Thr | Tyr | Ser | Thr | Tyr 270 | Gly | Lys |
| Phe | Leu | Ala 275 | Asp | Gly | Gly | Cys | Ser 280 | Gly | Gly | Ala | Tyr | Asp 285 | Ile | Ile | Ile |
| Cys | Asp 290 | Glu | Cys | His | Ser 295 | Thr | Asp | Ser | Thr | Thr 300 | Ile | Leu | Gly | Ile | Gly |
| Thr 305 | Val | Leu | Asp | Gln | Ala 310 | Glu | Thr | Ala | Gly | Ala 315 | Arg | Leu | Val | Val | Leu 320 |
| Ala | Thr | Ala | Thr | Pro 325 | Pro | Gly | Ser | Val | Thr 330 | Val | Pro | His | Pro | Asn 335 | Ile |
| Glu | Glu | Val | Ala 340 | Leu | Ser | Asn | Thr | Gly 345 | Glu | Ile | Pro | Phe | Tyr 350 | Gly | Lys |
| Ala | Ile | Pro 355 | Ile | Glu | Ala | Ile | Arg 360 | Gly | Gly | Arg | His | Leu 365 | Ile | Phe | Cys |
| His | Ser 370 | Lys | Lys | Lys | Cys 375 | Asp | Glu | Leu | Ala | Ala 380 | Lys | Leu | Ser | Gly | Leu |
| Gly 385 | Ile | Asn | Ala | Val | Ala 390 | Tyr | Tyr | Arg | Gly | Leu 395 | Asp | Val | Ser | Val | Ile 400 |
| Pro | Thr | Ile | Gly | Asp 405 | Val | Val | Val | Val | Ala 410 | Thr | Asp | Ala | Leu | Met 415 | Thr |
| Gly | Tyr | Thr | Gly 420 | Asp | Phe | Asp | Ser | Val 425 | Ile | Asp | Cys | Asn | Thr 430 | Cys | Val |
| Thr | Gln 435 | Thr | Val | Asp | Phe | Ser 440 | Leu | Asp | Pro | Thr | Phe 445 | Thr | Ile | Glu | Thr |
| Thr | Thr 450 | Val | Pro | Gln | Asp | Ala 455 | Val | Ser | Arg | Ser | Gln 460 | Arg | Arg | Gly | Arg |
| Thr 465 | Gly | Arg | Gly | Arg | Arg 470 | Gly | Ile | Tyr | Arg | Phe 475 | Val | Thr | Pro | Gly | Glu 480 |
| Arg | Pro | Ser | Gly | Met 485 | Phe | Asp | Ser | Ser | Val 490 | Leu | Cys | Glu | Cys | Tyr 495 | Asp |

```
Ala  Gly  Cys  Ala  Trp  Tyr  Glu  Leu  Thr  Pro  Ala  Glu  Thr  Ser  Val  Arg
               500                      505                      510

Leu  Arg  Ala  Tyr  Leu  Asn  Thr  Pro  Gly  Leu  Pro  Val  Cys  Gln  Asp  His
          515                      520                      525

Leu  Glu  Phe  Trp  Glu  Ser  Val  Phe  Thr  Gly  Leu  Thr  His  Ile  Asp  Ala
     530                      535                      540

His  Phe  Leu  Ser  Gln  Thr  Lys  Gln  Ala  Gly  Asp  Asn  Phe  Pro  Tyr  Leu
545                      550                      555                      560

Val  Ala  Tyr  Gln  Ala  Thr  Val  Cys  Ala  Arg  Ala  Gln  Ala  Pro  Pro  Pro
                565                      570                      575

Ser  Trp  Asp  Gln  Met  Trp  Lys  Cys  Leu  Ile  Arg  Leu  Lys  Pro  Thr  Leu
               580                      585                      590

His  Gly  Pro  Thr  Pro  Leu  Leu  Tyr  Arg  Leu  Gly  Ala  Val  Gln  Asn  Glu
               595                      600                      605

Val  Thr  Leu  Thr  His  Pro  Ile  Thr  Lys  Tyr  Ile  Met  Ala  Cys  Met  Ser
          610                      615                      620

Ala  Asp  Leu  Glu  Val  Val  Thr
625                      630
```

( 2 ) INFORMATION FOR SEQ ID NO:2:

( i ) SEQUENCE CHARACTERISTICS:
        ( A ) LENGTH: 54 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Ser  Thr  Trp  Val  Leu  Val  Gly  Gly  Val  Leu  Ala  Ala  Leu  Ala  Ala  Tyr
1                   5                        10                       15

Cys  Leu  Thr  Thr  Gly  Ser  Val  Val  Ile  Val  Gly  Arg  Ile  Ile  Leu  Ser
               20                       25                       30

Gly  Arg  Pro  Ala  Ile  Val  Pro  Asp  Arg  Glu  Leu  Leu  Tyr  Gln  Glu  Phe
               35                       40                       45

Asp  Glu  Met  Glu  Glu  Cys
               50
```

( 2 ) INFORMATION FOR SEQ ID NO:3:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= "Xaa at position 34 means
        Abu (2- Aminobutyric acid)"

( x i ) SEQUENCE DESCRIPTION: SEQ ID NO:3:

```
Gly  Ser  Val  Val  Ile  Val  Gly  Arg  Ile  Ile  Leu  Ser  Gly  Arg  Pro  Ala
1                   5                        10                       15

Ile  Val  Pro  Asp  Arg  Glu  Val  Leu  Tyr  Gln  Glu  Phe  Asp  Glu  Met  Glu
               20                       25                       30

Glu  Xaa
```

METHOD FOR REPRODUCING IN VITRO THE PROTEOLYTIC ACTIVITY OF THE NS3 PROTEASE OF HEPATITIS C VIRUS (HCV)

DESCRIPTION

This present invention has as its subject a method for reconstituting the serine protease activity associated with the HCV NS3 protein, which makes use of the ability of the HCV protein NS4A, or sequences contained therein, to act as a cofactor of the serine protease activity or more generally speaking of enzymatic activities associated with NS3.

As is known, the hepatitis C virus (HCV) is the main etiological agent of non-A, non-B hepatitis (NANB). It is estimated that HCV causes at least 90% of post-transfusional NANB viral hepatitis and 50% of sporadic NANB hepatitis. Although great progress has been made in the selection of blood donors and in the immunological characterization of blood used for transfusions, there is still a high level of acute HCV infection among those receiving blood transfusions (one million or more infections every year throughout the world). Approximately 50% of HCV-infected individuals develop cirrhosis of the liver within a period that can range from 5 to 40 years. Furthermore, recent clinical studies suggest that there is a correlation between chronic HCV infection and the development of hepatocellular carcinoma.

HCV is an enveloped virus containing an RNA positive genome of approximately 9.4 kb. This virus is a member of the Flaviviridae family, the other members of which are the flaviviruses and the pestiviruses. The RNA genome of HCV has recently been mapped. Comparison of sequences from the HCV genomes isolated in various parts of the world has shown that these sequences can be extremely heterogeneous. The majority of the HCV genome is occupied by an open reading frame (ORF) that can vary between 9030 and 9099 nucleotides. This ORF codes for a single viral polyprotein, the length of which can vary from 3010 to 3033 amino acids. During the viral infection cycle, the polyprotein is proteolytically processed into the individual gene products necessary for replication of the virus. The genes coding for HCV structural proteins are located at the 5'-end of the ORF, whereas the region coding for the non-structural proteins occupies the rest of the ORF.

The structural proteins consists of C (core, 21 kDa), E1 (envelope, gp$^{37}$) and E2 (NS1, gp61). C is a non-glycosylated protein of 21 kDa which probably forms the viral nucleocapsid. The protein E1 is a glycoprotein of approximately 37 kDa and it is believed to be a structural protein for the outer viral envelop. E2, another membrane glycoprotein of 61 kDa, is probably a second structural protein in the outer envelope of the virus.

The non-structural region starts with NS2 (p24), a hydrophobic protein of 24 kDa whose function is unknown. NS2, A protein of 68 kDa which follows NS2 in the polyprotein, is predicted to have two functional domains: a serine protease domain in the first 200 amino-terminal amino acids, and an RNA-dependent ATPase domain at the carboxy terminus. The gene region corresponding to NS4 codes for NS4A (p6) and NS4B (p26), two hydrophobic proteins of 6 and 26 kDa, respectively, whose functions have not yet been clarified. The gene corresponding to NS5 also codes for two proteins, NS5A (p56) and NS5B (p65), of 56 and 65 kDa, respectively. In amino acid sequence present in all the RNA-dependent RNA polymarases can be recognized within the NS5 regions. This suggests that the NS5 region contains parts of the viral replication machinery.

Various molecular biological studies indicate that the signal peptidase, a protease associated with the reticulum of the host cell, is responsible for proteolytic processing in the non-structural region, that is to say at sites C/E1, E1/E2 and E2/NS2. The serine protease contained in NS3 is responsible for cleavage at the junctions between NS3 and NS4A, between NS4A and NS4B, between NS4B and NS5A and between NS5A and NS5B. In particular it has been found that the cleavage performed by this serine protease leaves a residue of cysteine or threonine on the amino-terminal side (position P1) and an alanine or serine residue on the carboxy-terminal side (position P1') of the scissile bond. A second protease activity of HCV appears to be responsible for the cleavage between NS2 and NS3. This protease activity is contained in a region comprising both part of NS2 and the part of NS3 containing the serine protease domain, but does not use the same catalytic mechanism.

In the light of the above description, the NS3 protease is considered a potential target for the development of anti-HCV therapeutic agents. However, the search for such agents has been hampered by the evidence that the serine protease activity displayed by NS3 in vitro is too low to allow screening of inhibitors.

It has now been unexpectedly found that this important limitation can be overcome by adopting the method according to the present invention, which also gives additional advantages that will be evident from the following.

According to the present invention, the method to reproduce in vitro the proteolytic activity of the protease NS3 of HCV is characterized by using in the reaction mixture, both sequences contained in NS3 and sequences contained in NS4A.

Optimal serine protease activity is obtained when NS4A is present in a ration of 1:1 with NS3.

NS3 and NS4A can also be incorporated in the reaction mixture as NS3-NS4A precursor, as this precursor will generate, by means of an autoproteolytic agent, equimolar amounts of NS3 and NS4A.

It is also possible to mutate the site of cleavage between NS3 and NS4A, in a precursor, so that NS4A remains covalently bound to NS3. The sequences that do not influence the proteolytic activity of NS3 can subsequently be removed from this non-proteolyzable precursor.

The invention also extends to a new composition of matter, characterized in that it comprises proteins whose sequences are described in SEQ ID NO:1 and SEQ ID NO:2 or sequences contained therein or derived therefrom. It is understood that these sequences may vary in different HCV isolates, as all the RNA viruses show a high degree of variability. This new composition of matter has the proteolytic activity necessary to obtain the proteolytic maturation of several of the non-structural HCV proteins.

The present invention also has as its subject the use of these compositions of matter in order to prepare an enzymatic assay capable of identifying, for therapeutic purposes, compounds that inhibit the enzymatic activity associated with NS3, including inhibitors of the interaction between NS3 and NS4A.

Up to this point a general description has been given of the present invention. With the aid of the following examples, a more detailed description of specific embodiments thereof will now be given, in order to give a clearer understanding of its objects, characteristics, advantages and method of operation.

The figure illustrates plasmid vectors used in the method to activate the HCV NS3 protease in cultivated cells and in vitro (example 1 and example 2).

EXAMPLE 1

Method of Activation of HCV NS3 Serine Protease in Cultivated Cells

Plasmid vectors were constructed for expression of NS3, NS4A and other non-structural HCV proteins in HeLa-cells. The plasmids constructed are schematically illustrated in FIG. 1. Selected fragments of the cDNA corresponding to the genome of the HCV BK isolate (HCV—BK) were cloned downstream of the promoter of the bacteriophage T7 in the plasmid vector pCite-1$^R$ (Novagen). This expression vector contains the internal ribosome entry site of the encephalomyocarditis virus, so as to guarantee an effective translation of the messenger RNA transcribed from promoter T7, even in the absence of a CAP structure.

The various fragments of HCV—BK cDNA were cloned into the plasmid pCite-1$^R$ using methods known in molecular biology practice. pCite(NS3) contains the portion of the HCV—BK genome comprised between nucleotides 3351 and 5175 (amino acids 1007–1615 of the polyprotein). pCite(NS4B/5A) contains the portion of the HCV—BK genome comprised between the nucleotides 5652 and 7467 (amino acids 1774–2380). pCite(NS3/4A) contains the portion of the HCV—BK genome comprised between the nucleotides 3711 and 5465 (amino acids 991 and 1711). pCiteNS4A) contains the portion of the HCV—BK genome comprised between the nucleotides 5281 and 5465 (amino acids 1649–1711). pCite(NS5AB) contains the portion of the HCV—BK genome comprised between the nucleotides 6224 and 9400 (amino acids 1965–3010). The numbering given above agrees with the sequences for the genome and the polyprotein given for HCV—BK in Takamizawa et al, Structure and organization of the hepatitis C virus genome isolated from human carriers, (1991), J. Virol. 65, 1105–1113.

In order to obtain efficient expression of the various portions of the HCV polyprotein, the HeLa cells were infected with vTF7-3, a recombinant vaccinia virus which allows synthesis of the RNA polymerase of the bacteriophage T7 in the cytoplasm of infected cells. These cells, after infection, were then transfected with plasmid vectors selected from among those described in figure. The HeLa cells thus infected and transfected were then metabolically labelled with [$^{35}$S]methionine and the recombinant proteins encoded by the various plasmids could be identified by immunoprecipitation with polyclonal rabbit antibodies that recognize NS3, NS4 or NS5A. The method described in the present example for analysis of recombinant HCV proteins has already been described in L. Tomei et al, "NS3 is a serine protease required for processing of hepatitis C virus polyprotein", J. Virol. (1993) 67, 1017–1026 and in the bibliography mentioned therein.

By transfecting the plasmid pCite(NS3) into the HeLa cells infected with vTF7-3, it is possible to observe the synthesis of a protein containing the catalytic domain of the HCV NS3 protease. pCite(NS4B5A) coder for a portion of the HCV polyprotein containing a peptide bond, at the junction between NS4B and NS5B, which would be expected to be hydrolyzed by the serine protease activity associated with NS3. However, when pCiteNS3 is cotransfected with pCiteNS4B5A, there is no evidence of proteolytic cleavage. Conversely, when the NS3 serine protease domain is expressed in combination with NS4A the proteolytic cleavage of the precursor encoded by pCite (NS4B5A) can take place normally. Coexpression of the NS3 serine protease domain and 4A can be achieved, for example, by transfection with equimolar amounts of the plasmids pCite(NS3) and pCite(NS4A), by transfection of a plasmid coding for a precursor containing both NS3 and NS4A [pCite(NS34A)], or by transfection of a derivative of the latter plasmid to which all the sequences that are not relevant for proteolysis have been deleted [pCite (NS3Δint1237–1633)]. NS4A expressed transiently in HeLa cells can thus activate the proteolytic activity associated with NS3, which otherwise would not be seen.

EXAMPLE 2

Method for Activation of the HCV Serine NS3 Protease in an In Vitro Translation Assay The plasmids described in FIG. 1 can also be used for in vitro synthesis of mRNA coding for the respective HCV proteins using the purified RNA polymerase enzyme of the phage T7 (Promega).

Generally the plasmids derived from pCite-1$^R$ were linearized using suitable restriction enzymes and transcribed using the protocols supplied by the manufacturer (Promega). These synthetic mRNA, could later be used to synthesize the corresponding proteins in extracts of rabbit reticulocytes in the presence of canine pancreas microsomal membranes. The reticulocyte extracts, the canine pancreas microsomal membranes, like all the other material required, were purchased from Promega, which also supplied the instructions for the in vitro protein syntheses process described above.

Programming the in vitro translation mixture with mRNA transcribed from pCite(NS3) it is possible to observe synthesis of a protein with the expected molecular weight (68 kDa) containing the entire NS3 serine protease domain. The mRNA transcribed from pCite(NS5AB) guides the synthesis of a precursor of 115 kDa which contains NS5A and NS5B and is thus a substrate for the proteolytic activity associated with NS3.

However, when the two proteins, containing the NS3 serine protease domain and the substrate with the site corresponding to the junction between NS5A and NS5B, are synthesized in the same reaction mixture, there is no clear evidence of the proteolytic activity of NS3.

On the contrary, the mRNA transcribed from pCite (NS34A) is translated into a precursor protein of approximately 76 kDa which self-processes proteolytically in vitro to give equimolar amounts of two proteins of 70 kDa and 6 kDa, containing NS3 and NS4A, respectively.

If, in addition to the mRNA transcribed from pCite (NS34A), the mRNA transcribed from pCite(NS5AB) is included in the in vitro translation mixture, there can be observed, in addition to the self-proteolysis at the site between NS3 and NS4A, the generation of two new proteins of 56 kDA and 65 kDA which contain NS5A and NS5B, respectively. These proteins represent the product of proteolysis of the precursor containing NS5A and NS5B by NS3. Similarly, the 56 kDa and 65 kDa protein products, generated proteolytically from the NS5AB precursor, are obtained if the mRNA transcribed from pCite (NS3Δint1237–1635) is cotranslated with the mRNA translated from pCite(NS5AB).

This result can be summarized by stating that, in vitro, the protease domain of NS3 alone is not capable of exhibiting protease activity on a substrate containing NS5A and NS5B. However, the serine protease activity of NS3 becomes evident if another protein sequence containing NS4A is present in addition to the NS3 protease domain.

EXAMPLE 3

Method of Activation of the HCV NS3 Protease Using a Synthetic Peptide Containing NS4A Sequences A synthetic peptide containing the sequence SEQ ID NO:3 was synthesized on solid phase. This sequence is derived from the C-terminal portion of Seq ID NO:2. Synthesis of the peptide took place on solid phase according to processes known to those operating in this field. In this peptide, the carboxy terminal cysteine has been replaced with alpha-aminobutyric acid (Abu).

This peptide was added to an in vitro translation mixture simultaneously programmed with the mRNAs transcribed from the plasmids pCite(NS3) and pCite(NS5AB).

It was thus possible to observe the proteolytic activity associated with the serine protease domain of NS3, which resulted in the proteolytic cleavage of the substrate in the two products containing the proteins NS5A and NS5B. This activity is dependent on the simultaneous presence of the NS3 serine protease domain and the synthetic peptide with the sequence SEQ ID NO:3.

EXAMPLE 4

Method of Assay of a Recombinant HCV NS3 Serine Protease on a Peptide Substrate

The plasmid pT7-7 NS3(1027–1206), described in FIG. 1 and in Example 4, was constructed in order to allow expression in *E. coli* of the protein fragment comprised between amino acid 1 and amino acid 180 of SEQ. ID No:1. Such fragment contains the serine protease domain of NS3, as determined experimentally. The fragment of HCV cDNA coding for NS3 fragment just described was cloned in the pT7-7 plasmid, an expression vector that contains the T7 RNA polymerase promoter φ 10 and the translation start site for the T7 gene 10 protein (Studier and Moffatt, Use of bacteriophage T7 RNA polymerase to direct selective high-level expression of cloned genes, (1986), J. Mol Biol. 189, p. 113–130). The cDNA fragment coding for the NS3 serine protease domain as defined above was cloned downstream of the bacteriophage T7 promoter and in frame with the first ATG codon of the T7 gene 10 protein, using methods that are known to the molecular biology practice. The pT7-7 plasmid also contains the gene for the β-lactamase enzyme, which can be used as a marker of selection of *E. coli* cells transformed with plasmids derived with pT7-7.

The plasmid pT7—7 NS3(1027–1206) is then transformed in the *E. coli* strain BL21(DE53), which is normally employed for high-level expression of genes cloned into expression vectors containing T7 promoter. In this strain of *E. coli*, the T7 gene polymerase is carried on the bacteriophage λDE53, which is integrated into the chromosome of BL21. Expression from the gene of interest is induced by addition of isopropylthiogalactoside (IPTG) to the growth medium according to a procedure that has been previously described (Studier and Moffatt, Use of bacteriophage T7 RNA polymerase to direct selective high-level expression of cloned genes, (1986), J. Mol Biol- 189, p. 113–130).

The recombinant NS3 fragment containing the serine protease domain could be purified from *E. coli* BL21(DE53) transformed with the plasmid pT7-7 NS3(1027–1206) by the procedure summarized below.

In brief, *E. coli* BL21(DES3) cells harboring the pT7-7 NS3(1027–1206) plasmid were grown at 37° C. to an optical density at 600 nm of around 0.8 absorbance units. Thereafter, the medium was cooled down to 22° C. and production of the desired protein induced by addition of IPTG to a final concentration of 0.4 mM. After 4–6 hours at 22° C. in the presence of IPTG, cells were harvested and lysed by means of a French-pressure cell in a buffer containing 20 mM sodium phosphate pH 6.5, 0.5% (w/v) (3-[(3-cholamidopropyl)-dimethylammonio] 1-propanesulfonate (CHAPS), 50% (v/v) glycerol, 10 mM dithiothreitol and 1 mM EDTA (lysis buffer). The cell debris was removed by centrifugation (1 hour at 12000×g) and the resulting pellet resuspended in lysis buffer, digested with DNAse I, re-homogenized and re-centrofuged as described above. S-Sepharose Fast Flow ion exchange resin (Pharmacia) pre-equilibrated in lysis buffer was added to the pooled supernatants (30% v/v) and the slurry was stirred for 1 hour at 4° C. The resin was sedimented and washed extensively with lysis buffer and poured into a chromatography column. The NS3 protease was deluted from the resin by applying a 0–1M NaCl gradient. The protease-containing fractions equilibrated with 50 mM sodium phosphate buffer pH 7.5, 10% (v/v) glycerol, 0.5% (w/v) CHAPS and 2 mM dithiothreitol. The protein was 90–95% pure after this step. Purification to >98% was achieved by subsequent chromatography on Heparin Sepharose equilibrated with 50 mM Tris pH 7.5, 10% (v/v) glycerol, 0.5% (w/v) CHAPS and 2 mM dithiothreitol. Elution of the NS3 protease from this column was achieved by applying a linear 0–1M NaCl gradient.

The concentration of the purified protein was determined by the Bio-Rad protein assay (Bio-Rad cat. 500-0006).

The recombinant NS3 serine protease produced according to the above procedure in *E. coli* could be assayed for activity by cleaving a substrate that provides detectable cleavage products. The signal is preferably detectable by colorimetric or fluorometric means. Methods such as HPLC and the like are also suitable.

For example, we used, as a substrate, synthetic peptides corresponding to the NS4A/4B junction of the HCV polyprotein.

The activity assay is performed by incubating 5–1000 μM substrate and 0.05–1 μM protease in buffer containing 25 mM Tris/HCl pH 7.5, 3 mM dithiothreitol, 0.5% (w/v) CHAPS and 10% (v/v) glycerol for 1–3 hours at 22° C. The reaction is stopped by addition of trifluoracetic acid to yield a final concentration of 0.1% (w/v).

The reaction products are then separated by HPLC on a C18 reverse phase column and quantitated according to their absorbance of the far UV light.

The proteolytic activity displayed by recombinant NS3 serine protease purified from *E. coli* is very low when the activity assay is performed as described above. However, we found that increasing amounts of the synthetic peptide described in SEQ ID NO:3 stimulate the proleolytic activity of the recombinant NS3 serine protease up to 20-fold. Maximal activity is reached when the recombinant NS3 serine protease and the synthetic peptide are present in equimolar amounts.

The assay described above can be used for the search of protease inhibitors. Because the activity of NS3 protease in such assay depends on the interaction of the NS3 serine protease domain with amino acid sequences derived from NS4A, it is also possible, by using the assay described above, to search for antagonists of the interaction between NS3 and NS4A that will ultimately inhibit the proteolytic activity associated with NS3.

EXAMPLE 5

Detailed Construction of the Plasmids in the Sole Figure pCite(NS3) contains the portion of the HCV—BK genome comprised between nucleotides 3351 and 5175 (amino acids 1007–1615 of the polyprotein). Construction of this plasmid has been described in L. Tomei et al, "NS3 is a serine protease required for processing of hepatitis C virus polyprotein", J. Virol. (1993) 67, 1017–1026.

pCite(NS4B/5A) was obtained by cloning a ScaI-BamHI fragment derived from the plasmid pCite(NS4–5), described in Tomei et al, into pCite(NS3) that was previously digested with MscI and BamHI. pCite(NS4B/5A) contains the portion of the HCV genome comprised between nucleotides 5652 and 7467 (amino acids 1774–2380 of the polyprotein).

pCite(NS5AB) codes for a protein that comprises the sequence from amino acid 1965 to amino acid 3010 of the HCV—BK polyprotein. To construct this plasmid, the plasmid pCite(SX) described in Tomei et al (1993), supra, was first digested with AseI and treated with the Klenow fragment of the DNA polymerase. After inactivation of the Klenow enzyme, the plasmid was digested with XbaI. The resulting cDNA fragment, containing the region between nucleotides 6224 and 9400, was purified and inserted into the BstXI and XbaI sites of the vector pCite-1$^R$, after blunting the end generated by BstXI with T4 DA polymerase.

pCite(NS3/4A) was obtained as follows. A cDNA fragment, corresponding to the region between nucleotides 3711 and 5465 of the HCV—BK genome, was synthesized by means of polymerase chain reaction (PCR) using sequence-specific oligonucleotides as primers. A UAG stop codon was suitably included in the antisense oligonucleotide. After PCR amplification, the resulting cDNA was cleaved at the 5' end with SAlI and the product of 750 pairs of bases cloned directionally into the SalI and NheI sites of the plasmid pCite(SX), after blunt-ending the NheI end with the Klenow fragment of the DNA polymerase. The resulting plasmid codes for the portion of HCV—BK polyprotein comprised between amino acids 991 and 1711.

For the construction of pCite(NS4A), a cDNA fragment, corresponding to the region between the nucleotides 5281 and 5465 of the HCV-BK genome (amino acids 1649–1711), was obtained by polymerase chain reaction (PCR) amplification with sequence-specific oligonucleotides as primers. The cDNA resulting from the PCR amplification was subsequently cloned into the BstxI and StuI sites of the plasmid pCite-1$^R$, after blunt-ending the BstXI digested end with the DNA polymerase of the bacteriophage T4.

pCite(NS3Δint1237–1635) is a derivative of pCite(NS3/4A) from which all the sequences comprised between nucleotide 4043 and nucleotide 5235 have been deleted. It was obtained by digesting pCite(NS3/4A) with BstEII and partially with ScaI. The fragment containing the deletion of interest was then circularised by use of T4 DNA ligase. This plasmid codes for a protein that has the same amino- and carboxy-terminal ends as that encoded by pCite(NS3/4A), but all the amino acid residues comprised between amino acid 1237 and amino acid 1635, experimentally found to be dispensible for the serine protease NS3 activity, have been deleted.

pT7-7[NS3(1027–1206)] contains the HCV sequence from nucleotide 3411 to nucleotide 3951, encoding the HCV NS3 fragment comprised between amino acid 1027 and amino acid 1206. In order to obtain this plasmid, a DNA fragment was generated by amplification of HCV cDNA by the polymerase chain reaction (PCR). The cDNA fragment obtained by PCR was phosphorylated, digested with Nde I and subsequently cloned downstream of the bacteriophage T7 promoter, following immediately the first ATG codon of the T7 gene 10 protein in the vector pT7-7 previously digested with Nde I and Sma I (Studier and Moffatt, Use of bacteriophage T7 RNA polymerase to direct selective high-level expression of cloned genes, (1986), J. Mol. Biol. 189, p. 113–130). It is to note that an amber codon was inserted immediately following the HCV-derived sequence.

We claim:

1. A method for determining cofactor activity of a candidate compound comprising a fragment of hepatitis C virus (HCV) NS4A protein on HCV NS3 protease, comprising the steps of:

(a) providing a reaction mixture comprising NS3 protease and a NS3 protease substrate;

(b) introducing the candidate compound to the reaction mixture; and (c) measuring NS3 protease activity to determine whether an increase in protease activity has occurred.

2. The method according to claim 1, wherein the NS3 protease is a recombinant protein.

3. A method for determining HCV NS3 protease modulating activity of a candidate compound, comprising the steps of:

(a) providing a reaction mixture comprising HCV NS3 protease, HCV NS4A cofactor, and a NS3 protease substrate;

(b) introducing a candidate compound to the reaction mixture; and (c) measuring NS3 protease activity to determine whether modulation of protease activity has occurred.

4. The method according to claim 3, wherein the NS3 protease and the NS4A cofactor are recombinant proteins.

5. The method according to claim 3, wherein the NS3 protease and the NS4A cofactor are fused together as a single recombinant protein.

6. The method according to claim 5, wherein a proteolytic site of cleavage between the NS3 protease and the NS4A cofactor is mutated so as to be resistant to proteolytic cleavage between NS3 and NS4A.

7. The method according to claim 3, wherein the NS4A cofactor is a synthetic peptide.

8. The method according to claim 3, wherein the NS4A cofactor and NS3 protease are present in a ratio of approximately 1:1.

9. The method according to claim 3, where the modulation of protease activity is inhibition.

10. The method according to claim 9, wherein the NS3 protease has a sequence of SEQ ID NO:1 and the NS4A cofactor has a sequence of SEQ ID NO:2.

11. The method according to claim 3, wherein the NS3 protease has a sequence of SEQ ID NO:1 and the NS4A cofactor has a sequence of SEQ ID NO:2.

12. A method for determining modulating activity of a candidate compound on HCV NS3 protease/NS4A cofactor interaction, comprising the steps of:

(a) providing a reaction mixture comprising HCV NS3 protease, HCV NS4A cofactor, and a NS3 protease substrate.

(b) introducing a candidate compound to the reaction mixture; and (c) measuring NS3 protease activity to determine whether modulation of NS3 protease/NS4A cofactor interaction has occurred.

13. The method according to claim 12, wherein the NS3 protease and the NS4A cofactor are recombinant proteins.

14. The method according to claim 12, wherein the NS3 protease and the NS4A cofactor are fused together as a single recombinant protein.

15. The method according to claim 14, wherein a proteolytic site of cleavage between the NS3 protease and the NS4A cofactor is mutated so as to be resistant to proteolytic cleavage.

16. The method according to claim 12, wherein the NS4A cofactor is a synthetic peptide.

17. The method according to claim 12, wherein the modulation of NS3 protease/NS4A cofactor interaction is inhibition.

18. The method according to claim 17, further comprising a step of determining cofactor concentration dependence of the inhibition of NS3 protease/NS4A cofactor interaction.

19. The method according to claim 17, wherein the NS3 protease has a sequence of SEQ ID NO:1 and the NS4A cofactor has a sequence of SEQ ID NO:2.

20. The method according to claim 12, wherein the NS3 protease has a sequence of SEQ ID NO:1 and the NS4A cofactor has a sequence of SEQ ID NO:2.

* * * * *

UNITED STATES PATENT AND TRADEMARK OFFICE
CERTIFICATE OF CORRECTION

PATENT NO. : 5,739,002
DATED : April 14, 1998
INVENTOR(S) : Raffaele DE FRANCESCO et al.

It is certified that error appears in the above-identified patent and that said Letters Patent is hereby corrected as shown below:

Title page, item 73, change "Istituto di Richerche di Biologia Molecolare P. Angeletti S.p.A." to --Istituto di Ricerche di Biologia Molecolare P. Angeletti S.p.A.--.

Title page, item 75, change "Christina Failla" to --Cristina Failla--.

Signed and Sealed this

Third Day of August, 1999

Attest:

Q. TODD DICKINSON

Attesting Officer

Acting Commissioner of Patents and Trademarks